US00PP24724P3

(12) United States Plant Patent
James

(10) Patent No.: US PP24,724 P3
(45) Date of Patent: Aug. 5, 2014

(54) SHRUB ROSE PLANT NAMED 'PEJAMORE'

(50) Latin Name: *Rosa hybrida*
Varietal Denomination: PEJamore

(71) Applicant: Early Morning LLC, Pomona, CA (US)

(72) Inventor: Peter J. James, Trividale (GB)

(73) Assignee: Early Morning LLC, Pomona, CA (US)

( * ) Notice: Subject to any disclaimer, the term of this patent is extended or adjusted under 35 U.S.C. 154(b) by 105 days.

(21) Appl. No.: 13/694,425

(22) Filed: Nov. 30, 2012

(65) Prior Publication Data

US 2014/0157461 P1 Jun. 5, 2014

(51) Int. Cl.
*A01H 5/00* (2006.01)

(52) U.S. Cl.
USPC ..... Plt./103; Plt./101; Plt./102

(58) Field of Classification Search
USPC ..... Plt./130, 101, 102
See application file for complete search history.

(56) References Cited

U.S. PATENT DOCUMENTS

PP20,325 P3 9/2009 James

*Primary Examiner* — Susan McCormick Ewoldt
(74) *Attorney, Agent, or Firm* — McKee, Voorhees & Sease, P.L.C.

(57) ABSTRACT

A new variety of Shrub rose suitable for garden decoration, having flowers of ivory with a cranberry 'eye' coloration.

1 Drawing Sheet

Classification: The present invention relates to a new *Rosa hybrida* plant.

Variety denomination: The new plant has the varietal denomination 'PEJamore'.

BACKGROUND OF THE INVENTION

This invention relates to a new and distinct variety of Shrub Rose. It has as its seed parent the variety known as 'PEJamblu' (U.S. Plant Pat. No. 20,325) and an undisseminated seedling of my creation as its pollen parent with the following genetic origin {'SCRivbell'×(Tigris×Baby Love)}.

SUMMARY OF THE INVENTION

Among the features which distinguish the new variety from other presently available and commercial rose cultivars known to the inventor are the following combinations of characteristics: it's unusual ivory with a cranberry 'eye' flower coloration, its excellent color stability throughout the life of the flower, it's very vigorous growth and its bushy spreading tall growing habit. The plant has a bushy spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'PEJamore' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'PEJamblu' by the following combination of characteristics: whereas 'PEJamore' bears small flowers (about 3.0 to about 3.5 cm. in diameter) of ivory coloration with a cranberry 'eye', 'PEJamblu' bears significantly larger flowers (about 7.5 to about 10.0 cm. in diameter) of mauve/lilac ageing to slate blue coloration. The new variety is classified as a Shrub rose with a bushy spreading tall growing habit (about 165 to about 200 cm. in height), whereas the seed parent has a compact upright significantly shorter growing habit (about 90 to about 120 cm. in height).

The new variety may be distinguished from its pollen parent, an undisseminated seedling of my creation by the following combination of characteristics: whereas 'PEJamore' bears small flowers (about 3.0 to about 3.5 cm. in diameter) of ivory coloration with a cranberry 'eye', the undisseminated seedling bears significantly larger flowers (about 4.5 to about 6.5 cm. in diameter) of yellow coloration with a reddish 'eye'. The new variety is classified as a Shrub rose with a bushy spreading tall growing habit (about 165 to about 200 cm. in height), whereas the pollen parent has a rounded bushy and compact significantly shorter growing habit (about 65 to about 85 cm. in height).

COMPARISON WITH THE CLOSEST COMMERCIALLY AVAILABLE CULTIVAR

The new variety may be distinguished from its closest commercially available cultivar, 'SPRolempink' U.S. Plant Pat. No. 23,581 by the following combination of characteristics: whereas 'PEJamore' bears double flowers (about 10 to 15 petals) of ivory coloration with a cranberry 'eye', 'SPRolempink' bears flowers of light pink fuchsia coloration with a magenta center and with significantly lesser petalage (about 8 to 10 petals). The new variety has a bushy spreading tall growing habit (about 165 to about 200 cm. in height), whereas the closest commercially available cultivar has a bushy compact significantly shorter growing habit (about 90 to about 135 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety bears medium sized flowers in pyramidal shaped clusters of three to fifteen per stem. Flowers are borne on strong, medium length stems (about 40 to about 88 cm with a diameter of 0.5 to 0.7 cm.). Outdoors, the plant blooms abundantly and nearly continuously during the growing season. The flowers have a moderate fruity to citrus-like fragrance.

BUD

The bud is about 1.0 to 1.2 cm. long and about 0.8 to 0.9 cm. in diameter when the petals start to unfurl. The bud is short and pointed ovoid in shape. As the petals open (after the calyx breaks), the bud is about 1.2 to about 1.4 cm. in diameter at the widest point, about 1.5 to about 1.9 cm. in length, and moderately ovoid in form. When the sepals first divide, the bud color is 20E. When half blown, the upper sides of the petals are 14D in color and the lower sides of the petals are 14D.

The sepals are about 3.0 cm. in length and about 0.9 cm. in width at the widest point. The color of the sepal is 138B on the upper surface and is 146A on the lower surface. The outer surface of the sepal is smooth and bears about 2 foliaceous appendages. The inner surface of the sepal is covered with fine wooly tomentum; sepal margins are lined with very few stipitate glands and hairs.

The peduncle is stiff and erect, medium in length (about 4.0 cm.), and of average caliper (about 0.2 cm. in diameter). It is rough, prickly and glandular. Peduncle color is 146A often with an overlay of 184B.

The receptacle of the flower is funnel shaped and medium in size (about 0.5 cm. in length and about 0.8 cm. in diameter). Its surface is smooth. The receptacle color is 146B often with an overlay of 184B.

BLOOM

When fully open, the bloom ranges from about 3.0 cm. to about 3.5 cm. in diameter. Petalage is double with about 10 to 15 petals under normal conditions. When first open, the bloom form is cupped and the petals are loosely cupped with petal edges somewhat reflexed outward. The bloom flattens over time.

PETALS

The substance of the petals is thick and leathery with a smooth surface. The petals are about 2.6 to about 3.4 cm. in length and about 2.6 cm. to about 3.6 cm. in width at the widest point. The shape of the petals is round to obcordate and flat with obtuse to obcordate apices. Petal margins are entire. Petals are arranged in an imbricated fashion and drop off of the plant cleanly before dying. Petals last on the plant for about 5 days. As a cut flower the petals last about 6 days.

Petaloids number from 1 to 5 and are 14D in color. Petaloids are about 1.9 to about 3.2 cm. in length and about 1.0 to about 2.4 cm. in width at the widest point. Petaloids are irregularly shaped somewhat obovate to oblanceolate with rounded apices.

NEWLY OPENED FLOWER

The upper side of the petals are 14D in color on the newly opened flower. The reverse side of the petals are 14D in color. The base of the petals has a large color spot of about 0.7 cm. to 0.8 cm by about 0.7 cm. to 0.8 cm. with a color of 46B. The under and upper surface colors of the petaloids are similar in coloration to the upper and under surfaces of the petals.

The general tonality at the end of the first day is no change.

THREE-DAY-OLD FLOWER

At the end of the third day the tonality is generally fading from 14D in color to 158D in color. The base color spot changes from 46B in color to 60C in color. The under and upper surface colors of the petaloids are similar in coloration to the upper and under surfaces of the petals.

MALE REPRODUCTIVE ORGANS

Stamens average about 45 to 50 in number and are about 0.8 to 0.9 cm. in length. Anthers are 0.3 cm. in length with color of 21B. Anthers are arranged regularly around the styles and mixed with petaloids.

Filaments are of somewhat long length (about 0.6 cm. to about 0.7 cm.) most with anthers. Filaments are 184C in color. Pollen is abundant and is 165C in color.

FEMALE REPRODUCTIVE ORGANS

Pistils vary in number (average about 30). Styles are moderately even, average in length (about 0.4 cm.) moderately heavy in caliper, and bunched. Style color is 184C.

Stigmas are 156C in color and 0.1 cm in length. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 11 cm. long and 9 cm. wide.

The terminal leaflets are pointed oval in shape. The base is rounded oblique in shape and the apex shape is acuminate. The upper side of the leaves is leathery and glossy with a single serrated edge. The terminal leaflets are about 4.8 to about 5.9 cm. in length and about 2.8 to about 3.7 cm. in width at the widest point New foliage is 175A in color on the upper side and is 175A in color on the lower side. Old foliage is 137A on the upper side and is 138B on the lower side.

The vein color of the leaves is 146C and the venation patter is reticulate.

The rachis is average in caliper and rough. The upper side is shallowly grooved with many hairs and few stipitate glands on the edges of the grooves. The underside of the rachis is rough with some hairs and few small prickles. The rachis color is 138B.

The stipules are about 1.5 cm. in length, of medium width (about 0.4 cm.) and serrated. The auricle is subulate in shape. The stipules color is 138B.

The petiole is average in caliper and rough. The upper side is shallowly grooved with many hairs and few stipitate glands on the edges of the grooves. The underside of the petiole is rough with some hairs and few small prickles. The petiole is about 0.3 to about 0.9 cm. in length and about 0.1 to about 0.2 cm in width at the widest point. The petiole color is 138B.

The plant displays an above average degree of resistance to rust, downy mildew and black spot and an average degree of resistance to powdery mildew as compared to other commercial varieties grown under comparable conditions in Pomona, Calif. The plant's winter hardiness and drought/heat tolerance are yet to be determined.

GROWTH

The plant has a bushy spreading tall growing habit (about 165 to about 200 cm. in height and about 185 to about 205 cm. spread at the widest point), with full branching. It displays very vigorous growth and the canes are of somewhat heavy caliper for the class (about 2.1 to about 3.2 cm. in diameter at the widest point).

Stems of new wood are 183B in color. Stems of old wood are 137C in color. The new wood and the old wood bear some large prickles. The Prickles are moderately hooked downward with a short narrow oval base. Prickles are of 0.7 cm in length. Young prickles are 178B in color. When mature prickles are 200C in color.

There are no small prickles on the main stalk or lateral stalks.

I claim:

1. A new and distinct Shrub rose plant of the variety substantially as described and illustrated herein.

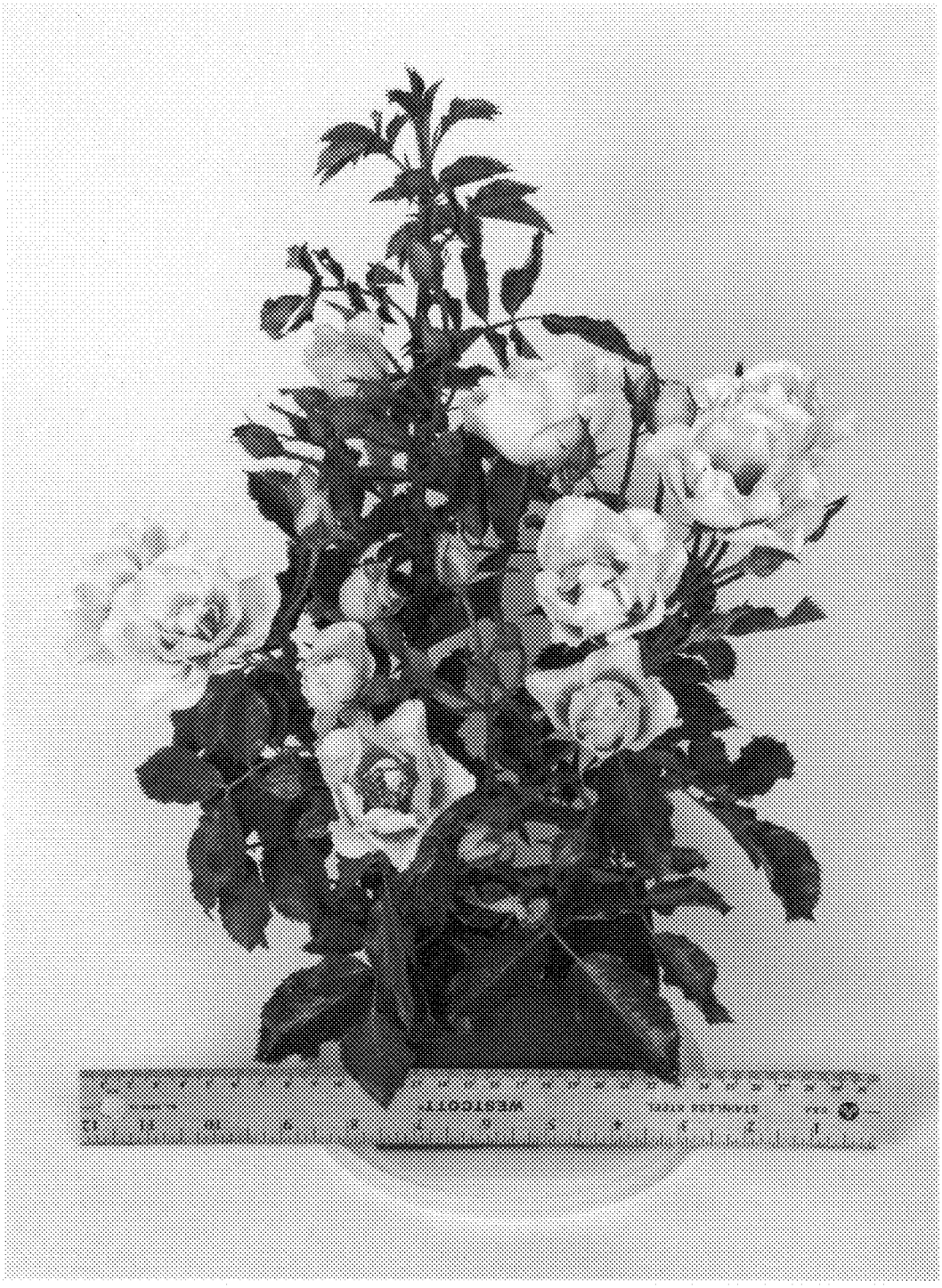

* * * * *